United States Patent
Brown

(10) Patent No.: US 6,440,972 B1
(45) Date of Patent: Aug. 27, 2002

(54) HETEROCYCLIC COMPOUNDS USEFUL AS OXIDO-SQUALENE CYCLASE INHIBITORS

(75) Inventor: George Robert Brown, Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/367,400

(22) PCT Filed: Feb. 9, 1998

(86) PCT No.: PCT/GB98/00405

§ 371 (c)(1),
(2), (4) Date: Aug. 13, 1999

(87) PCT Pub. No.: WO98/35956

PCT Pub. Date: Aug. 20, 1998

(30) Foreign Application Priority Data

| Feb. 13, 1997 | (GB) | ............................................... 9702946 |
| Jul. 26, 1997 | (GB) | ............................................... 9715734 |
| Sep. 11, 1997 | (GB) | ............................................... 9719237 |

(51) Int. Cl.⁷ ........................ C07D 401/14; A61K 9/14; A61P 31/496

(52) U.S. Cl. .................................. 514/252.11; 544/357

(58) Field of Search ........................ 514/227.8, 252.11; 544/357

(56) References Cited

U.S. PATENT DOCUMENTS

| 4,167,567 A | 9/1979 | McCall ........................ 424/250 |
| 4,231,938 A | 11/1980 | Monaghan et al. ...... 260/343.5 |
| 4,537,896 A | 8/1985 | Claeson et al. ............. 514/330 |
| 4,564,610 A | 1/1986 | Rahtz et al. |
| 4,629,728 A | 12/1986 | Regnier et al. |
| 4,788,196 A | 11/1988 | Cross et al. ................. 514/252 |
| 4,806,536 A | 2/1989 | Cross et al. ................. 514/252 |
| 4,835,165 A | 5/1989 | Cross et al. |
| 4,840,963 A | 6/1989 | Shepard et al. |
| 4,968,704 A | 11/1990 | Cross et al. |
| 5,032,604 A | 7/1991 | Baldwin et al. |
| 5,138,058 A | 8/1992 | Geisen et al. ............... 344/295 |
| 5,254,563 A | 10/1993 | Huth et al. |
| 5,332,822 A | 7/1994 | Misra ........................ 546/164 |
| 5,364,865 A | 11/1994 | Diana |
| 5,371,091 A | 12/1994 | Misra et al. ................. 514/314 |
| 5,411,971 A | 5/1995 | Emonds-Alt et al. ....... 514/318 |
| 5,556,977 A | 9/1996 | Wayne et al. |
| 5,563,141 A * | 10/1996 | Wayne et al. ................ 514/252 |
| 5,580,881 A | 12/1996 | Binet et al. .................. 514/307 |
| 5,606,065 A | 2/1997 | Emonds-Alt et al. ....... 546/223 |
| 5,681,954 A | 10/1997 | Yamamoto et al. ......... 544/114 |
| 5,795,893 A | 8/1998 | Bondinell et al. .......... 514/252 |
| 5,856,326 A | 1/1999 | Anthony et al. ............ 514/252 |
| 6,022,869 A | 2/2000 | Faull ....................... 514/227.8 |
| 6,037,343 A | 3/2000 | Ali ............................. 514/252 |
| 6,090,813 A * | 7/2000 | Waterson et al. ........... 514/255 |
| 6,225,309 B1 * | 5/2001 | Faull et al. ................. 514/218 |

FOREIGN PATENT DOCUMENTS

| AU | 10177/92 | 7/1992 |
| DE | 39 05 364 A1 | 8/1990 |
| DE | 39 43 225 A | 6/1991 |
| DE | 42 43 858 A1 | 6/1994 |
| DE | 43 06 506 A1 | 9/1994 |
| EP | 0 097 630 A2 | 1/1984 |
| EP | 0 232 740 A1 | 8/1987 |
| EP | 0 233 051 | 8/1987 |
| EP | 0 244 115 | 11/1987 |
| EP | 0 308 337 | 3/1989 |
| EP | 0 324 421 A2 | 7/1989 |
| EP | 0 359 389 | 3/1990 |
| EP | 0 352 946 A1 | 10/1990 |
| EP | 0 409 413 | 1/1991 |
| EP | 0 495 750 | 7/1992 |
| EP | 0 515 240 A1 | 11/1992 |
| EP | 0 519 449 A1 | 12/1992 |
| EP | 0 555 824 A1 | 8/1993 |
| EP | 0 576 941 A1 | 1/1994 |
| EP | 0 608 759 A2 | 8/1994 |
| FR | 2 697 252 A1 | 4/1994 |
| GB | 1 449 100 | 9/1976 |

(List continued on next page.)

OTHER PUBLICATIONS

Brown, G.R. et al, J. Med. Chem., 43, 2000, 4964–4972.*
Boissier et al., "Synthesis and Pharmacological Study of New Piperazine Derivatives. I. Benzylpiperazines", J. Med. Chem., Sep. 1963, pp. 541–544.
Caulkett et al., Chemical Abstracts; vol. 131:322629.
Conway et al., "Approaches to the Generation of 2,3–Indolyne"; Heterocycles. 1992, 34(11) 2095–2108.

(List continued on next page.)

Primary Examiner—Mukund J. Shah
Assistant Examiner—Thomas McKenzie
(74) Attorney, Agent, or Firm—Morgan, Lewis & Bockius LLP

(57) ABSTRACT

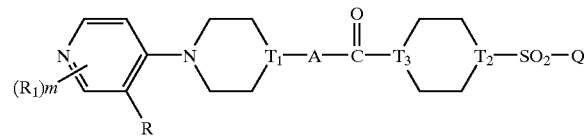

This invention concerns heterocyclic derivatives of formula (I) which are useful in inhibiting oxido-squalene cyclase, processes for their preparation and pharmaceutical compositions containing them. The present invention is also concerned with heterocyclic derivatives capable of inhibiting cholesterol biosynthesis and hence the lowering cholesterol levels in blood plasma. The present invention also relates to methods of using such heterocyclic derivatives in diseases and medical conditions such as hypercholesterolemia and atherosclerosis.

14 Claims, No Drawings

FOREIGN PATENT DOCUMENTS

| WO | WO 92/08709 | | 5/1992 |
|---|---|---|---|
| WO | WO 92/18478 | | 10/1992 |
| WO | WO 93/06085 | | 4/1993 |
| WO | WO 94/18185 | | 8/1994 |
| WO | WO 94/20467 | | 9/1994 |
| WO | WO 94/20468 | | 9/1994 |
| WO | WO 94/22835 | | 10/1994 |
| WO | WO 96/05189 | | 2/1996 |
| WO | WO 96/10022 | * | 4/1996 |
| WO | 96 10022 | | 4/1996 |
| WO | WO 96/26196 | | 8/1996 |
| WO | WO 96/30343 | | 10/1996 |
| WO | WO 96/33171 | | 10/1996 |
| WO | WO 97/06802 | * | 2/1997 |
| WO | 97 06802 | | 2/1997 |
| WO | WO 97/28128 | | 8/1997 |
| WO | WO 97/28129 | | 8/1997 |
| WO | WO 97/29104 | | 8/1997 |
| WO | WO 97/30971 | | 8/1997 |
| WO | WO 98/06705 | | 2/1998 |
| WO | WO 98/21188 | | 5/1998 |

OTHER PUBLICATIONS

Deratani et al., "Synthesis of new dialkylaminopyridine acylation catalysts and their attachment to insoluble polymer supports", Polymer, Apr. 1987, pp. 825–830.

Hibino et al.; "N–Phenylsulfonylindole derivatives", Chemical Abstracts, 118:147461, Apr. 1993.

Jain et al., "Compounds Acting on the Central Nervous System, VII. Studies in 1–Pyridyl–1–substituted Piperazines. A New Class of Anticonvulsants", J. Med. Chem., Sep. 1967, pp. 812–818.

Kataoka et al., Chemical Abstracts, vol. 123, No. 14, Oct. 2, 1995 Columbus, Ohio, US: abstract No. 179521d, "Homopiperazines as cell migration inhibitors." Xp002081582 see abstract & JP 95 145060 A (Tejin Ltd).

Kobayashi et al., Chemical Abstracts, vol. 130:296694.

Kobayashi et al., Chemical Abstracts, vol. 132:194391.

Nowak et al., Chemical Abstracts, vol. 131:337034.

Prasad et al., "Antiamoebic Action of Drugs and Synthetic Compounds Against Trophozoites of Entamoeba Histolytica Under Axenic and Polyxenic Culture Conditions and in the Infected Rat Caecum", Curr. Sci., Aug. 1984, pp. 778–781.

Ratouis et al., "Synthesis and pharmacological Study of New Piperazine Derivatives, II. Phenethylpiperazines", J. Med. Chem., Jan. 1965, pp. 104–107.

Sato et al., "Synthetic Studies on Cardiovascular Agents. III. Synthesis of Pyrano–[2,3–c]pyrazoline Derivatives", Yakugaku Zasshi, vol. 98(3), 1978, pp. 335–348.

Saxena et al., "Quantitative Structure Activity Relationship in 3–4 Disubstituted Pyridines & I–(3"–Amino–4"–pyridyl)–4–arylpiperazines" Indian J. Chem. vol. 19B, Oct. 1980, pp. 873–878.

Sundberg et al. "Synthesis with N–Protected 2–Lithiondoles"; J. Org. Chem., 1973 38(19) 3324–3330.

Take et al., Chemical Abstracts, vol. 133:58814.

Tawada et al., Chemical Abstracts, vol. 130:38404.

Tawada et al., Chemical Abstracts, vol. 131:170361.

Von G. Krüger, et al.; (Thomae et al.) Arzneim.–Fosch., Synthesen von N–Benzyl–aminocarbonsäuren und thren Derivaten; (Synthesis and N–benzylaminocarboxylic acids and their derivatives), vol. 23(2a), pp. 290–295.

Yokoyama et al. "Palladium–catalyzed cross–coupling reaction: direct allylation of aryl bromides with allyl acetate" Tetrahedron Letters., vol. 26, No. 52—1985 pp. 6457–6460, XP002081581 Oxford GB * p. 6458–6459: compound 7.

Zaoral et al., "Amino acids and peptides. LIX. Synthesis and some biological properties of L–DABB–vasopressin", Collect. Czech. Chem. Commun., vol. 31, 1966, pp. 90–95, XP002081879 see compound 11, p. 95.

Bowers Nemia et al., "Synthetic Routes to 3–Pyrrolidinol", Synth. Comm., 13(13):1117–1123 (1983).

Chambers et al., "Preparation of arylpyridine compounds for treating leukotriene–related diseases", Chemical Abstracts, Abstract No. 139113, vol. 119 (1993).

Cross et al., "Preparation of N–[(heterocyclicyl-methoyx)phenyl] sulfamides and analogs as antiarrhythmics", Chemical Abstracts, Abstract No. 231211, vol. 113 (1989).

Kato et al., "Reactivities of 4–Chloropyridine Derivatives and Their 1–Oxides", Chem. Pharm. Bull., 15:1343–1348 (1967).

Kato et al., "Studies on Ketene and Its Derivatives. LXXVI. [1)] Reactions of Acetoacetamide and β–Aminocrotonamide with β–Diketone, β–Ketoaldehyde and Related Compounds", Chem. Pharm. Bull., 24(2):303–309 (1976).

Kettner et al., "The Selective Inhibition of Thrombin by Peptides of Boroarginine", The Journal of Biological Chemistry, vol. 265, No. 30, pp. 18289–18297 (1990).

Mitsunobu et al., "Preparation of Carboxylic Esters and Phosphoric Esters by the Activation of Alcohols", Bull. Chem. Soc. Jpn., 44(12):3427–3430 (1971).

Smith et al., "Fibrin, Red Cell and Platelet Interactions in an Experimental Model of Thrombosis", Br. J. Pharmac., vol. 77, pp. 29–38 (1982).

Szmant et al., "Concerning the Variable Character of the Sulfone Group", J. Amer. Chem. Soc., vol. 78, pp. 3400–3403 (1956).

Vigroux et al., "Cyclization–Activated Prodrugs: N–(Substituted 2–hydroxyphenyl and 2–hydroxypropyl)carbamates Based on Ring–Opened Derivatives of Active Benzoxazolones and Oxazolidones as Mutual Produrgs of Acetamiophen", J. Med. Chem., vol. 38, pp. 3983–3994 (1995).

Vogel et al., "Comparison of Two Experimental Thrombosis Models in Rats Effects of Four Glycosaminoglycans", Thrombosis Research, vol. 54, No. 5, pp. 399–410 (1989).

Budavari: Merck Index, vol. 11 ED., 1989, See Monograph Nos. 804 and 2807.

Cattel et al: "Drug design based on biosynthetic studies: synthesis, biological activity, and kinetics of new inhibitors of 2,3–oxidosualene cyclase and squalene epoxidase.", Steroids., vol. 53, No. 3–5, 1989, pp. 363–391, XP000611661.

E. Jucker, "Uber C–substituierte Piperazinderativate", Helv. Chim. Acta., 45:2382–2042 (1962).

Sartori et al., "Synthesis and analgesic activities of urea derivatives of α–amino–N–pyridyl benzene propanamide", Eur J. Med Chem (1994), 431–439.

Tabacik et al: "Squalene epoxidase, oxido–squalene cyclase and cholesterol biosynthesis in normal and tumoral mucosa of the human gastrointestinal tract. Evidence of post–HMGCoA regulation.", Biochim. Biophys. Acta, vol. 666, No. 3, 1982, pp. 433–441, XP000610864.

* cited by examiner

HETEROCYCLIC COMPOUNDS USEFUL AS OXIDO-SQUALENE CYCLASE INHIBITORS

This application is the national phase of international application PCT/GB98/00405 filed Feb. 9, 1998 which designated the U.S.

This invention concerns heterocyclic derivatives which are useful in inhibiting oxido-squalene cyclase, processes for their preparation and pharmaceutical compositions containing them. The present invention is also concerned with heterocyclic derivatives capable of inhibiting cholesterol biosynthesis and hence in lowering cholesterol levels in blood plasma. The present invention also relates to methods of using such heterocyclic derivatives in diseases and medical conditions such as hypercholesterolemia and atherosclerosis.

There is evidence that high serum cholesterol levels are an important risk factor in coronary heart disease and associated diseases such as atherosclerosis and ischaemic heart disease. As a result there has been a great deal of interest in finding ways of lowering cholesterol levels in blood plasma. Although it has been possible to obtain some reduction by means of diet only modest reductions in cholesterol levels in blood plasma have been obtained. Consequently, there is a need for therapeutic approaches to reducing cholesterol levels.

Several different classes of compounds have been reported to possess the ability to lower cholesterol levels in blood plasma. For example agents which inhibit the enzyme 3-hydroxy-3-methyl glutaryl CoA (HMGCoA) reductase, which is essential for the production of cholesterol, have been reported to reduce levels of cholesterol in blood plasma (serum cholesterol). Illustrative of this class of compounds is the HMGCoA reductase inhibitor known as lovastatin which is disclosed in U.S. Pat. No 4,231,938. Other agents which are reported to lower serum cholesterol include those which act by complexing with bile acids in the intestinal system. Such agents act by sequestering bile acids within the intestinal tract resulting in a lowering of the levels of bile acid circulating in the enterohepatic system. This in turn promotes replacement of bile acids, which are synthesised in the liver from cholesterol. This results in an upregulation of the hepatic LDL cholesterol receptor and in a consequential lowering of circulating blood cholesterol levels.

The biosynthesis of cholesterol is a complex process which will be considered here as three principal stages, namely 1) the conversion of acetic acid to mevalonic acid 2) the conversion of mevalonic acid to squalene and 3) the conversion of squalene to cholesterol. In the last stage, squalene is first converted into 2,3-oxido-squalene and then to lanosterol. Lanosterol is then converted to cholesterol through a number of enzymatic steps.

The conversion of 2,3-oxido-squalene to lanosterol is a key step in the biosynthesis of cholesterol. This conversion is catalysed by the enzyme oxido-squalene cyclase. It follows that inhibition of this enzyme decreases the amount of lanosterol available for conversion to cholesterol. Consequently, inhibition of oxido-squalene cyclase should interupt cholesterol biosynthesis and give rise to a lowering of cholesterol levels in blood plasma.

The present invention is based on the discovery that certain heterocyclic derivatives are inhibitors of oxido-squalene cyclase and are hence useful in treating diseases and medical conditions in which inhibition of oxido-squalene cyclase is desirable.

According to the present invention there is provided a compound of formula I (set out hereinafter together with the other formulae referred to herein in a separate sheet following the Examples), or a pharmaceutically-acceptable acceptable salt thereof, wherein:

R is selected from halogeno, cyano, nitro, carboxy, (1–6C)alkyl, (1–6C)alkoxy, (1–6C)alkanoyl, (1–6C) alkoxycarbonyl and halogeno(1–6C)alkyl;

$R_1$ is selected from hydrogen, amino, halogeno, cyano, nitro, carboxy, (1–6C) alkyl, (1–6C)alkoxy, (1–6C) alkanoyl, (1–6C)alkoxycarbonyl, halogeno(1–6C) alkyl, N-(1–6C)alkylamino, N,N-di-[(1–6C)alkyl] amino, (1–6C)alkylthio, (1–6C)alkylsulphinyl and (1–6C)alkylsulphonyl;

m is 1 or 2;

A is selected from a direct bond and (1–4C)alkylene;

$T_1$ is selected from N and $CR_2$, wherein $R_2$ may be hydrogen, (1–4C)alkyl, (2–4C)alkenyl or (2–4C) alkynyl (preferably $R_2$ is hydrogen);

$T_2$ is selected from N and CH;

$T_3$ is selected from N and $CR_2$, wherein $R_2$ is as defined above; provided that when $T_2$ is CH then $T_3$ is not $CR_2$ and when $T_1$ is $CR_2$ then $T_3$ is not $CR_2$;

wherein the heterocyclic ring containing $T_1$ and the heterocyclic ring containing $T_2$ may, independently, be optionally substituted by one or more substituents selected from (1–6C)alkyl, (1–6C)alkoxy, phenyl (1–4C)alkyl, halogeno and (1–6C)alkoxycarbonyl;

Q is selected from phenyl, naphthyl, phenyl(1–6C)alkyl, phenyl(2–6C)alkenyl and a heteroaryl moiety containing up to 3 heteroatoms selected from nitrogen, oxygen and sulphur;

and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C) cycloalkyl, (3–6C)cycloalkyl(1–4C)alkyl, (1–4C) alkylenedioxy, (1–6C)alkylamino, N,N-di-[(1–6C) alkyl]amino, N-(1–6C)alkylcarbamoyl, di-N[(1–6C) alkyl]carbamoyl, (1–6C)alkanoylamino, (1–6C) alkoxycarbonyl, (1–6C)alkylthio, (1–6C) alkylsulphinyl, (1–6C)alkylsulphonyl, halogeno(1–6C) alkyl, (1–6C)alkanoyl and a heteroaryl group comprising a 5- or 6-membered monocyclic heteroaryl ring containing up to three heteroatoms selected from nitrogen, oxygen and sulphur.

The compounds of the present invention are oxido-squalene cyclase inhibitors and hence possess the property of inhibiting cholesterol biosynthesis. There is provided as a feature of the invention a compound of formula I (as hereinbefore defined), or a pharmaceutically-acceptable salt thereof, for use in medical therapy. Also provided is the use of a compound of formula I (as hereinbefore defined), or a pharmaceutically-acceptable acceptable salt thereof, for the manufacture of a medicament for treating diseases or medical conditions in which inhibition of oxido-squalene cyclase is desirable. There is also provided the use of a compound of formula I (as hereinbefore defined), or a pharmaceutically-acceptable acceptable salt thereof, for the manufacture of a medicament for inhibiting cholesterol biosynthesis. The compounds of the present invention will be useful in treating diseases or medical conditions in which an inhibition of oxido-squalene cyclase is desirable, for example those in which a lowering of the level of cholesterol in blood plasma is desirable. In particular, the compounds of the present invention will be useful in treating hypercholesterolemia and/or ischaemic diseases associated with atheromatous vascular degeneration such as atherosclerosis.

Thus the present invention also provides the use of a compound of formula I (as hereinbefore defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

Thus according to a further feature of the present invention there is provided a method of inhibiting oxido-squalene cyclase in a warm-blooded animal (such as man) requiring such treatment, which method comprises administering to said animal an effective amount of a compound of formula I (as hereinbefore defined), or a pharmaceutically-acceptable salt thereof. In particular, the present invention provides a method of inhibiting cholesterol biosynthesis, and more particularly to a method of treating hypercholesterolemia and atheromatous vascular degneration (such as atherosclerosis).

In particular, the compounds of the present invention are potentially useful in inhibiting cholesterol biosynthesis in man and hence in treating the above-mentioned medical conditions in man.

It will be understood that when a compound of formula I contains a chiral centre, it may exist in, and be isolated in, an optically active or racemic form. The invention includes any optically active or racemic form of a compound of formula I which possesses the beneficial pharmacological effect of inhibiting oxido-squalene cyclase. The synthesis of optically active forms may be carried out by standard techniques of organic chemistry well known in the art for example by, resolution of a racemic form, by synthesis from optically active starting materials or by asymmetric synthesis. It will be appreciated that certain compounds of formula I may exist as geometrical isomers. The invention includes any geometrical isomer of a compound of formula I which possesses the beneficial pharmacological effect of inhibiting oxido-squalene cyclase.

It will also be understood that certain compounds of the present invention may exist in solvated, for example hydrated, as well as unsolvated forms. It is to be understood that the present invention encompasses all such solvated forms which possess the property of inhibiting oxido-squalene cyclase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "tert-butyl" being referred to specifically when intended.

Particular values for R include, for example, for halogeno; chloro, bromo, iodo or fluoro, particular values are chloro, bromo and iodo;

for alkyl; (1–4C)alkyl, such as methyl, ethyl, propyl, iso-propyl, butyl, iso-butyl, sec-butyl or tert-butyl;

for alkoxy; metoxy, ethoxy, propoxy, iso-propoxy, butoxy, pentoxy or 3-methylbutoxy;

for alkoxycarbonyl; (1–4C)alkoxycarbonyl, such as, methoxycarbonyl, ethoxycarbonyl, propoxycarbonyl, iso-propoxycarbonyl, butoxycarbonyl or tert-butoxycarbonyl;

for halogenoalkyl halogeno(1–4C)alkyl such as halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluoromethyl, difluoromethyl and fluoromethyl;

for alkanoyl; formyl, acetyl, propionyl and butynyl;

Particular values for $R_1$ include, for example, for halogeno; chloro, bromo or iodo;

for alkyl; (1–4C)alkyl, such as methyl, ethyl, propyl, iso-propyl, butyl, iso-butyl, sec-butyl or tert-butyl;

for alkoxy; methoxy, ethoxy, propoxy, iso-propoxy, butoxy, pentoxy or 3-methylbutoxy;

for alkoxycarbonyl; (1–4C)alkoxycarbonyl such as methoxycarbonyl, ethoxycarbonyl; propoxycarbonyl, iso-propoxycarbonyl, butoxycarbonyl or tert-butoxycarbonyl;

for halogenoalkyl; halogeno(1–4C)alkyl such as halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluoromethyl, difluoromethyl and fluoromethyl;

for N-alkylamino; N-(1–4C)alkylamino, such as, N-methylamino, N-ethylamino, N-propylamino or N-butylamino;

for N,N-di-[alkyl]amino; N,N-di-[(1–4C)alkyl]amino, such as N,N-dimethylamino, N,N-diethylamino, N-methyl-N-ethylamino, N-methyl-N-propylamino or N,N-dipropylamino;

for alkylthio; methylthio, ethylthio, propylthio, iso-propylthio or butylthio;

for alkylsulphinyl; methylsulphinyl, ethylsulphinyl, propylsulphinyl, iso-propylsulphinyl or butylsulphinyl;

for alkylsulphonyl; methylsulphonyl, ethylsulphonyl, propylsulphonyl, iso-propylsulphonyl or butylsulphonyl;

for alkanoyl; formyl, acetyl, propionyl and butyryl;

Particular values for optional substituents on the heterocyclic rings containing $T_1$ and $T_2$ include, for example, for alkyl; (1–4C)alkyl such as methyl, ethyl, propyl, isopropyl, butyl, iso-butyl, sec-butyl or tert-butyl;

for alkoxy; (1–4C)alkoxy such as methoxy, ethoxy, propoxy, iso-propoxy or butoxy;

for phenylalkyl; phenyl (1–2C)alkyl such as benzyl, 2-phenylethyl or 1-phenylethyl for halogeno; fluoro, chloro, bromo or iodo for alkoxycarbonyl; methoxycarbonyl, ethoxycarbonyl, iso-propoxycarbonyl or butyoxycarbonyl;

Particular values for optional substituents which may be present on Q include, for example, for alkyl; (1–4C)alkyl, such as methyl, ethyl, propyl, iso-propyl, butyl, iso-butyl, sec-butyl or tert-butyl;

for cycloalkyl cyclopropyl, cyclobutyl or cyclopentyl;

for cycloalkylalkyl (3–6C)cycloalkyl(1–2C)alkyl such as cyclopropylmethyl, cyclopropylethyl, cyclobutylmethyl or cyclopentylmethyl;

for alkenyl; (2–2C)alkenyl, such as allyl, prop-1-enyl, 2-methyl-2-propenyl or 2-butenyl;

for alkynyl; (2–2C)alkynyl, such as prop-2-ynyl or but-2-ynyl;

for alkoxy; (1–6C)alkoxy, such as methoxy, ethoxy, propoxy, iso-propoxy, butoxy, pentoxy or 3-methylbutoxy;

for alkylamino; (1–4C)alkylamino, such as methylamino, ethylamino, propylamino or butylamino;

for N,N-di-[alkyl]amino; N,N-di-[(1–4C)alkyl]amino such as N,N-dimethylamino, N,N-diethylamino, N-methyl-N-propylamino or N,N-dipropylamino;

for N-alkylcarbamoyl; N-(1–4C)alkylcarbamoyl such as N-methylcarbamoyl, N-ethylcarbamoyl, N-propylcarbamoyl, N-butylcarbamoyl or N-tert-butylcarbamoyl or (N-(2-methylpropyl)carbamoyl;

for N,N-di-[alkyl]carbamoyl; N,N-di-[(1–4C)alkyl] carbamoyl, N,N-dimethylcarbamoyl or N,N-diethylcarbamoyl;

alkoxycarbonyl; (1–4C)alkoxycarbamoyl such as methoxycarbonyl, ethoxycarbonyl, propoxycarbonyl, iso-propoxycarbonyl, butoxycarbonyl or tert-butoxycarbonyl;

for alkylthio; (1–4C)alkylthio such as methylthio, ethylthio, propylthio, iso-propylthio or butylthio;

for alkylsulphinyl; (1–4C)alkylsulphinyl such as methylsulphinyl, ethylsulphinyl, propylsulphinyl, iso-propylsulphinyl or butylsulphinyl;

for alkylsulphonyl; (1–4C)alkylsulphonyl such as methylsulphonyl, ethylsulphonyl, propylsulphonyl, iso-propylsulphonyl or butylsulphonyl;

for halogeno; fluoro, chloro, bromo or iodo;

for halogenoalkyl; halogeno(1–4C)alkyl such as halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluromethyl, difluoromethyl and fluoromethyl;

for alkanoylamino; (1–4C)alkanoylamino such as formamido, acetamido, propionamido, iso-propionamido, butyramido and iso-butyramido;

for alkylenedioxy; methylenedioxy or ethylenedioxy;

for alkanoyl; (1–4C)alkanoyl such as formyl, acetyl, propionyl or butyryl;

In general, it is preferred, that $R_1$ is hydrogen and m is 1.

In general, it is preferred that R is selected from halogeno, trifluoromethyl and cyano. More preferably, R is halogeno such as chloro, bromo or fluoro.

In general, it is preferred, for example, that A is a direct bond.

In general, the heterocyclic rings containing $T_1$ and $T_2$ will be unsubstituted or bear one or two substituents selected from those hereinbefore defined.

In general it is preferred, for example, that Q is phenyl, naphthyl or phenyl(2–6C)alkenyl (such as styryl) or a 5- or 6-membered heteroaryl moiety as herein before defined (such as thienyl). More preferably, Q is phenyl.

In general, Q will be unsubstituted or will bear one, two or three (preferably one or two) substituents selected from those hereinbefore defined.

Particular values for Q when it is a heteroaryl moiety which comprises a 5- or 6-membered heteroaryl moiety which is fused to one or two benzo rings are, for example, benzofuranyl, benzothienyl, quinolyl, isoquinolyl, quinoxalinyl, quinazolinyl, cinnolinyl, indolyl, indazolyl, benzoxazolyl and benzothiazolyl which may be attached through any available position including through any available nitrogen atom.

Particular values for Q, or subsituted on Q, when either or both are a heteroaryl which comprises a 5- or 6-membered monocyclic heteroaryl ring are, for example, furyl, thienyl, pyridyl, pyrazinyl, pyrimidinyl, pyridazinyl, pyrrolyl, pyrazolyl, oxazolyl, isoxazolyl, thiazolyl, isothiazolyl, 1,2,3-triazolyl, 1,2,4-triazolyl, oxadiazolyl, furazanyl, tetrazolyl and thiadiazolyl which may be attached through any available position including through any available nitrogen atom.

A particular value for Q when it is naphthyl is, for example, 1-naphthyl or 2-naphthyl.

A particular value for Q when it is phenylalkyl is, for example, phenyl(1–2C)alkyl, such as benzyl, 2-phenylethyl or 1-phenylethyl.

A particular value for Q when it is phenylalkenyl, for example, phenyl(2–4C)alkenyl such as styryl, cinnamyl or 3-phenylprop-2-enyl.

Specific values for optional substituents on the heterocyclic ring containing $T_1$ or the heterocyclic ring containing $T_2$ include, for example (1–6C)alkyl (such as methyl) and (1–6C)alkoxycarbonyl (such as methoxycarbonyl or ethoxycarbonyl).

Specific values for optional substituents for Q include, for example, halogeno (such as fluoro, chloro, bromo or iodo), (1–6C)alkoxy (such as methoxy or ethoxy), (1–6C)alkyl (such as methyl, iso-propyl or t-butyl), halogeno(1–6C)alkyl (such as trifluoromethyl), N,N-di-[(1–4C)alkyl]amino (such as N,N-dimethylamino), nitro, cyano, and (1–6C) alkanoylamino (such as acetylamino).

Specific values for $R_1$ include, for example, hydrogen, amino, (1–6C)alkyl (such as methyl) and halogeno (such as chloro or bromo). More preferably $R_1$ is hydrogen.

Specific values for R include, for example, halogeno, such as bromo or chloro, and halogeno(1–6C)alkyl, such as trifluoromethyl.

In a particular embodiment, the heterocyclic rings containing $T_1$ and $T_2$ are unsubstituted.

In a particular embodiment there is provided a compound of formula I, or a pharmaceutically-acceptable acceptable salt thereof, wherein $T_1$ is selected from CH and N;

R is selected from halogeno, cyano, and trifluoromethyl, preferably halogeno;

$R_1$ is hydrogen, amino, halogeno, cyano, nitro, carboxy, (1–6C)alkanoyl, (1–6C)alkyl, (1–6C)alkoxy, (1–6C) alkoxycarbonyl, halogeno(1–6C)alkyl, N-(1–6C) alkylamino, N,N-di-[(1–6C)alkyl]amino, (1–6C) alkylthio, (1–6C)alkylsulphinyl and (1–6C) alkylsulphonyl, preferably hydrogen;

m is 1 or 2, preferably 1;

A is a direct bond;

$T_2$ is selected from CH and N;

$T_3$ is selected from CH and N; provided that when $T_2$ is CH then $T_3$ is not CH and when $T_1$ is CH then $T_3$ is not CH;

wherein the heterocyclic ring containing $T_1$ and the heterocyclic ring containing $T_2$ may, independently, be optionally substituted by one or more substituents selected from (1–6C)alkyl, (1–6C)alkoxy, phenyl (1–4C)alkyl, halogeno and (1–6C)alkoxycarbonyl;

Q is selected from phenyl, naphthyl, and phenyl(2–6C) alkenyl, preferably phenyl;

and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C) cycloalkyl, (3–6C)cycloalkyl(1–4C)alkyl, (1–4C) alkylenedioxy, (1–6C)alkylamino, N,N-di-[(1–6C) alkyl]amino, N-(1–6C)alkylcarbamoyl, N,N-di-[(1–6C)alkyl]carbamoyl, (1–6C)alkanoylamino, (1–6C)alkoxycarbonyl, (1–6C)alkylthio, (1–6C) alkylsulphinyl, (1–6C)alkylsulphonyl, halogeno(1–6C) alkyl, (1–6C)alkanoyl and a heteroaryl group comprising a 5- or 6-membered monocyclic ring containing up to three heteroatoms selected from nitrogen, oxygen and sulphur, preferably halogeno.

Further particular embodiments of the present invention include the following in which A is a direct bond or methylene, R is selected from halogeno, cyano and trifluoromethyl, $R_1$ and m are as hereinbefore defined, the rings containing $T_1$ and $T_2$ are optionally substituted as hereinbefore defined, and $T_1$, $T_2$, $T_3$ and Q are as defined in any one of the following groups:

(i) $T_1$=CH, $T_2$=$T_3$=N, Q=phenyl;
(ii) $T_1$=CH, $T_2$=$T_3$=N, Q=naphthyl;
(iii) $T_1$=CH, $T_2$=$T_3$=N, Q=phenyl(2–6C)alkenyl (such as styryl);
(iv) $T_1$=CH, $T_2$=$T_3$=N, Q=5- or 6-membered heteroaryl such as thienyl;
(v) $T_1$=N, $T_2$=CH, $T_3$=N, Q=phenyl;
(vi) $T_1$=N, $T_2$=CH, $T_3$=N, Q=naphthyl;
(vii) $T_1$=N, $T_2$=CH, $T_3$=N, Q=phenyl(2–6C)alkenyl (such as styryl);
(viii) $T_1$=N, $T_2$=CH, $T_3$=N, Q=5- or 6-membered heteroaryl such as thienyl;
(ix) $T_1$=$T_2$=$T_3$=N, Q=phenyl;
(x) $T_1$=$T_2$=$T_3$=N, Q=naphthyl:
(xi) $T_1$=$T_2$=$T_3$=N, Q=phenyl(2–6C)alkenyl (such as styryl); or
(xii) $T_1$=$T_2$=$T_3$=N, Q=5- or 6-membered heteroaryl such as thienyl, and wherein Q is preferably unsubstituted or substituted by one or two substituents independently selected from halogeno (such as bromo, fluoro or chloro), (1–6C)alkyl (such as methyl) and (1–6C) alkoxy (such as methoxy) or is a halogeno(1–6C)alkyl (such as trifluromethyl).

More particular embodiments include those in which A is a direct bond, R is halogeno, $R_1$ is H, m is 1, the rings containing $T_1$ and $T_2$ are unsubstituted, or $R_1$ is hydrogen or (1–6C)alkyl and m is 1 or 2 (preferably 1), and $T_1$, $T_2$, $T_3$ and Q are as defined in any one of the following groups:

(i) $T_1$=CH, $T_2$=$T_3$=N, Q=phenyl;
(ii) $T_1$=CH, $T_2$=$T_3$=N, Q=naphthyl;
(iii) $T_1$=CH, $T_2$=$T_3$=N, Q=phenyl(2–6C)alkenyl (such as styryl);
(iv) $T_1$=CH, $T_2$=$T_3$=N, Q=5- or 6-membered heteroaryl such as thienyl;
(v) $T_1$=N, $T_2$=CH, $T_3$=N, Q=phenyl;
(vi) $T_1$=N, $T_2$=CH, $T_3$=N, Q=naphthyl;
(vii) $T_1$=N, $T_2$=CH, $T_3$=N, Q=phenyl(2–6C)alkenyl (such as styryl);
(viii) $T_1$=N, $T_2$=CH, $T_3$=N, Q=5- or 6-membered heteroaryl such as thienyl;
(ix) $T_1$=$T_2$=$T_3$=N, Q=phenyl;
(x) $T_1$=$T_2$=$T_3$=N, Q=naphthyl:
(xi) $T_1$=$T_2$=$T_3$=N, Q=phenyl(2–6C)alkenyl (such as styryl); or
(xii) $T_1$=$T_2$=$T_3$=N, Q=5- or 6-membered heteroaryl such as thienyl, and wherein Q is preferably unsubstituted or substituted by one or two substituents independently selected from halogeno (such as bromo, fluoro or chloro), (1–6C)alkyl (such as methyl) and (1–6C) alkoxy (such as methoxy) or is a halogeno(1–6C)alkyl (such as trifluromethyl).

In a further embodiment R is selected from halogen (1–6C)alkyl, nitro, carboxy, (1–6C)alkanoyl and (1–6C)alkoxycarbonyl; and $R_1$, m, A, $T_1$, $T_2$, $T_3$ and Q are as hereinbefore defined.

In a specific embodiment, $T_2$ is N, $T_1$ is CH, $T_3$ is N or $T_2$ is N, $T_1$ is N and $T_3$ is CH, R is chloro or bromo, $R_1$ is hydrogen or (1–6C)alkyl, m is 1 or 2 and Q is phenyl optionally substituted by halogeno, (1–6C)alkyl or (1–6C)alkoxy.

Compounds of special interest include those described in the accompanying examples and their pharmaceutically-acceptable acceptable salts and are hence provided as a further feature of the present invention The compounds of formula I and their pharmaceutically-acceptable acceptable salts may be prepared by processes known to be applicable to the preparation of structurally related compounds. These procedures are illustrated by the following representative processes in which the various groups and radicals such as $R_1$, m, $T_1$, A, $T_2$, $T_3$, and Q are as hereinbefore defined (unless stated otherwise), and are provided as a further feature of the present invention. In cases where the compounds contain a group such as an amino, hydroxy, or carboxy group, this group may be protected using a conventional protecting group which may be removed when desired by conventional means.

(a) When $T_3$ is N, reacting an acid of formula II, or a reactive derivative thereof, with an amine of formula III.

A suitable reactive derivative of an acid of formula II is, for example, an acyl halide such as an acyl chloride formed by the reaction of the acid with an inorganic acid chloride such as thionyl chloride. Further suitable reactive derivatives include a mixed anhydride such as an anhydride formed by the reaction of the acid with a chloroformate such as iso-butyl chloroformate; an active ester such as an ester formed by the reaction of the acid and a phenol such as pentafluorophenol, an ester such as pentafluorophenyl trifluoroacetate or an alcohol such as N-hydroxybenzotriazole or N-hydroxysuccinimide; an acylazide, for example an azide formed by the reaction of the acid and an azide as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide. sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperture in the range, for example, –78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

(b) When $T_2$ is N, reacting an amine of formula IV, with a compound of formula Z—$SO_2$—Q in which Z is a displaceable group.

The reaction will, in general, be conveniently carried out in the presence of a suitable base. Suitable bases are those mentioned in (a) above.

A suitable value for the displaceable group Z is, for example, a halogeno or sulphonyloxy group, for example a fluoro, chloro, bromo, mesyloxy or 4-tolylsulphonyloxy group.

The reaction is conveniently performed in a suitable inert solvent or diluent as defined hereinbefore and at a temperature in the range, for example, 0° to 150° C., conveniently at or near ambient temperature.

(c) When $T_1$ is N, and wherein A is a direct bond, reacting a compound of formula V with an acid of formula VIII or a reactive derivative thereof.

The reaction will, in general, be carried out in the presence of a suitable base as mentioned in (a) above.

The reaction is conveniently performed in a suitable inert solvent or diluent as defined hereinbefore and at a temperature in the range, for example 0° to 150° C., conveniently at or near ambient temperature.

(d) Reacting a compound of formula VI in which Z is a displaceable group with an amine of formula VII.

The reaction will, in general, be carried out in the presence of a suitable base as mentioned in (a) above.

Suitable values for Z are those mentioned in (b) above.

The reaction is conveniently carried out in a suitable inert solvent as mentioned in (a) above and at a temperature in the range, for example 0° C. to 150° C., conveniently in the range 15° C. to 100° C.

(e) For those compounds of formula I in which R is a halogeno, halogenating the corresponding compound of formula I in which R is hydrogen.

In particular, the halogenation may be carried out using a N-halosuccinimide (eg. N-bromosuccinimide, N-chlorosuccinimide or N-iodosuccinimide). These halogenations may conveniently be carried out at 0° to 100° C. in a polar solvent such as tetrahydrofuran, methanol, dimethylformamide or acetonitrile.

Intermediate compounds of formula I where R is hydrogen also have activity against the enzyme oxido-squalene cyclase and may also be used in treating or preventing diseases and conditions mentioned above.

As mentioned above, it will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups are mentioned under (a) above. The protecting groups may be removed at any convenient stage in the synthesis using conventional techniques well known in the chemical art.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, allkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

When an optically active form of a compound of the formula I is required, it may be obtained, for example, by carrying out one of the aforesaid procedures using an optically active starting material or by resolution of a racemic form of said compound using a conventional procedure.

The beneficial pharmacological properties of the compounds of the present invention may be demonstrated using one or more of the following techniques.

(a) In vitro Test to Measure Inhibition of Oxido-squalene Cyclase

This test measures the inhibition of microsomal oxido-squalene cyclase in vitro by compounds at set concentrations in the incubation medium.

Microsomes are prepared from rat liver according to methods known in the art, for example, the method described in published European Patent Application No 324,421 and stored in liquid nitrogen prior to assay. Assay vials are kept at 37° C. throughout the incubation. The microsomes typically contain 15–20 mg of protein per ml of microsomes. For the assay, 1 ml of microsomes are diluted by the addition of 722 µl of 50 mM phosphate buffer pH 7.4.

Phosphate buffered Tween® 80 (polyoxyethylene sorbitan monolaurate) is prepared by adding 0.1 g Tween® 80 to 100 ml of 50 mM phosphate buffer.

A stock solution of oxido-squalene is made up as a solution in ethanol (0.65 mg.ml.$^{-1}$). 18 µl of radio-labelled oxido-squalene (1 µCi.ml$^{-1}$) is evaporated to dryness under a stream of nitrogen and redissolved in 1 ml of ethanol and 1 ml of the stock solution of oxido-squalene is added.

The test compound is dissolved in dimethyl sulphoxide to give a $10^{-1}$M stock solution. Dilutions are made from the stock to give $10^{-5}$M, $10^{-6}$M etc.

Phosphate buffered Tween® 80 (28 µl) is placed in 5 ml disposable plastic vials and 4 µl of the solution of the test compound is added and mixed well. An aliquot of the oxido-squalene mix (15 µl) is added and the vials pre-incubated for 10 minutes at 37° C. A portion of the microsomes (14.6 µl) are then added and incubated for a further 1 hour. The reaction is stopped by the addition of 315 µl of a mixture of 16% KOH in 20% ethanol.

The samples are then placed in a water bath at 80° C. for 2 hours to saponify. At the end of this process water (630 µl) is added followed by hexane (5 ml). The samples are tumble mixed for 5 minutes and then centrifuged. The hexane phase is removed and evaporated under nitrogen. The samples are then reconstituted in 300 µl of a 80:20 mixture of acetonitrile:iso-propyl alcohol. The samples are then chromatographed using a Hichrom® 30DsS1 column with an isocratic elution using a 95:5 mixture of acetonitrile:isopropyl alcohol and a flow rate of 1 ml.min$^{-1}$. The output from the UV detector is connected to a radio-chemical detector to visualise radiolabelled sterols. Reaction rate is measured as the conversion of oxido-squalene to lanosterol, and the effects of test compounds are expressed as an inhibition of this process.

By way of example, the compound described in Example 1 gave about 79% inhibition of rat microsomal oxido-squalene cyclase at a concentration of 0.01 µM.

(b) In vivo Test to Measure Inhibition of Oxido-squalene Cyclase

The ability of a compound to inhibit oxido-squalene cyclase and/or inhibit cholesterol biosynthesis may be assessed by a routine laboratory procedure carried out in the rat. The test involves administration of the compound to rats on a reversed lighting regimen. Female rats (35–55 g) are housed in reverse lighting conditions (red light from 0200 h–400 h) for a period of about 2 weeks prior to test. Animals are allowed free access to chow and drinking water throughout this period. At test, animals should weigh 100–140 g. The rats are dosed orally with the compound (typically 10–50 mg/kg) formulated in a polyethylene glycol/hydroxypropylmethyl cellulose mix. After 1 hour the rats are given triturated sodium mevalonate (15 µCi.kg$^{-1}$) intraperitoneally. Two hours after administration of the compound the rats are terminated and a piece of liver removed and weighed. The tissue is saponified at 80° C. for 2 hours in an ethanolic/potassium hydroxide solution (80% w/v aqueous KOH diluted 1:10 with ethanol). Water (2 ml) is added and the mixture extracted with iso-hexane (2×5 ml). The organic extracts are combined, evaporated to dryness under a stream of nitrogen and the residue is dissolved in a mixture of acetonitrile/iso-propanol (300 µl). An aliquot (200 µl) of this solution is loaded onto a HPLC column to separate the sterols. The radio-label content of each fraction is assessed using a radio chemical flow detector. Inhibitors of oxido-squalene cyclase are classed as those compounds which cause a build up of substrate and a concomitant disappearance of cholesterol and its precursors.

By way of example, the compound described in Example 1 below gave about 79% inhibition of rat cholesterol biosynthesis when dosed at 2 mg.kg$^{-1}$.

No overt toxicity was detected when compounds of the formula I were administered at several multiples of their minimum inhibitory dose or concentration.

When used in the treatment of diseases and medical conditions such as those mentioned above it is envisaged that a compound of formula I, or a pharmaceutically-acceptable acceptable salt thereof, will be administered orally, intravenously, or by some other medically acceptable route so that a dose in the general range of, for example, 0.01 to 10 mg per kg body weight is received. However it will be understood that the precise dose administered will necessarily vary according to the nature and severity of the disease, the age and sex of the patient being treated and the route of administration.

In general, the compounds of formula I, or a pharmaceutically-acceptable salt thereof, will usually be administered in the form of a pharmaceutical composition, that is together with a pharmaceutically-acceptable acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration; in the form of suppository for rectal administration: in the form of a sterile solution or suspension for parenteral administration such as by intravenous or intramuscular injection.

A composition may be obtained by conventional procedures using pharmaceutically-acceptable acceptable diluents and carriers well known in the art. Tablets and capsules for oral administration may conveniently be formed with a coating, such as an enteric coating (for example, one based on cellulose acetate phthalate), to minimise dissolution of the active ingredient of formula I, or a pharmaceutically-acceptable salt thereof, in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease.

Compounds which have the same general formula as formula I but in which R is hydrogen are described in published PCT patent application No. WO 96/10022. This reference also describes the prepartion of intermediates useful in the preparation of compounds of formula I in general and in particular to some of the compounds described below.

The invention will now be illustrated by the following non-limiting Examples in which, unless otherwise stated:

(i) evaporations were carried out by rotary evaporation in vacuo, (ii) operations were carried out at room temperature, that is in the range 18–26° C.;

(iii) flash column chromatography or medium pressure liquid chromatography (MPLC) was performed on silica gel (Merck Kieselgel Art.9385, obtained from E Merck, Darmstadt, Germany);

(iv) yields are given for illustration only and are not necessarily the maximum attainable by diligent process development;

(v) proton NMR spectra were normally determined at 200 MHz using tetramethylsilane (TMS) as an internal standard, and are expressed as chemical shifts (delta values) obtained in DMSO-$d_6$ (unless stated otherwise) in parts per million relative to TMS using conventional abbreviations for designation of major peaks: s, singlet; m, multiplet; t, triplet; br, broad; d, doublet; and (vi) all end-products were characterised by microanalysis, NMR and/or mass spectroscopy.

EXAMPLE 1

N-Chlorosuccinimide (150 mg) was added to a stirred suspension of 1-(4-bromophenylsulphonyl)-4-[1-(4-pyridyl)piperidin-4-ylcarbonyl]piperazine (493 mg) in acetonitrile (200 ml) at 25° C. The mixture was stirred for 18 hours. The acetonitrile was removed by evaporation. Water (20 ml) was added to the mixture and the aqueous phase was extracted with dichloromethane (2×25 ml). The organic extracts were combined, dried and evaporated. The residue was purified by chromatography on silica gel using a mixture of dichloromethane:methanol: 0.88 ammonia (96:3:1) as eluent to give 1-(4-bromophenylsulphonyl)-4-[1-(1-(3-chloro-4-pyridyl)piperidin-4-ylcarbonyl]piperazine as a colourless foam (381 mg): $^1$HNMR (CDCl$_3$): 1.70–1.80(m, 2H), 1.92–2.08(m, 2H), 2.53–2.62(m, 1H), 2.71–2.81(m, 2H), 3.02(br, 4H), 3.57–3.80(m, 6H), 6.78(d, 1H), 7.61(d, 2H), 7.70(d, 2H), 8.25(d, 1H), 8.38(s, 1H): MS.EI m/z 527 (M+H).

1-(4-Bromophenylsulphonyl)-4-[1-(4-pyridyl)piperidin-4-ylcarbonyl]piperazine used as starting material was prepared as described in published International Patent Application No. WO96/10022 (see, in particular Example 41 compound no. 1).

EXAMPLE 2

Using an analogous procedure to that described in Example 1 (using N-bromo or N-chlorosuccinimide as halogenating agent) the following compounds (1–9) were prepared.

TABLE 1

| Compd no | R | T$_1$ | T$_3$ | R$_1$ | W | m.p. (° C.) | $^1$H NMR (CDCl$_3$) |
|---|---|---|---|---|---|---|---|
| 1 | Br | CH | N | H | 4-Br | 137 | 1.7–1.82(m, 2H), 2.0(m, 2H), 2.58(m, 1H), 2.75 (td, 2H), 3.02(bs, 4H), 3.68(m, 6H), 6.8(d, 1H), 7.62(d, 2H), 7.7(d, 2H), 8.32(d, 1H), 8.58(s, 1H) |
| 2 | Cl | CH | N | CH$_3$ | 4-Br | 139 | 1.56–1.78(m, 2H), 1.89(m, 2H), 2.46(s, 3H), 2.68 (m, 1H), 3.02(m, 6H), 3.68(m, 4H), 4.41(d, 2H), 7.41(d, 2H), 7.52(d, 2H), 8.2(s, 1H) |
| 3 | Cl | N | CH | H | 4-Br | 156 | 1.75(m, 2H), 2.0(m, 2H), 2.58(m, 1H), 2.76(m, 2H), 3.04(bs, 4H), 3.69(m, 6H), 6.79(d, 1H), 7.61 (d, 2H), 7.70(d, 2H), 8.28(d, 1H), 8.39(s, 1H) |
| 4 | Br | CH | N | CH$_3$ | 4-Br | 105 | 1.70(m, 2H), 1.90(m, 2H), 2.48(s, 3H), 2.65(m, 1H), 2.93(m, 2H), 3.10(m, 4H), 3.70(m, 4H), 4.37 (d, 2H), 7.59(d, 2H), 7.70(d, 2H), 8.28(s, 1H) |
| 5 | Cl | CH | N | H | 3-F | 192 | 1.75(m, 2H), 2.0(m, 2H), 2.60(m, 1H), 2.78(m, 2H), 3.05(bs, 4h), 3.68(m, 6H), 6.79(d, 1H), 7.35 (m, 1H), 7.47(m, 1H), 7.55(m, 2H), 8.28(d, 1H), 8.39(s, 1H) |
| 6 | Cl | CH | N | H | 4-F | foam | 1.75(m, 2H), 2.0(m, 2H), 2.60(m, 1H), 2.78(m, 2H), 3.04(bs, 4H), 3.68(m, 6H), 6.79(d, 1H), 7.27(m, 2H), 7.78(m, 2H), 8.28(d,1H), 8.39(s, 1H) |
| 7 | Cl | CH | N | H | 4-OMe | foam | 1.75(m, 2H), 2.0(m, 2H), 2.57(m, 1H), 2.76(td, 2H), 3.04(bs, 4H), 3.66(m, 6H), 3.83(s, 3H), 6.78(d, 1h), 7.02(d, 2H), 7.68(d, 2H), 8.26(d, 1H), 8.39(s, 1H) |
| 8 | Cl | CH | N | H | 4-CH$_3$ | 164 | 1.75(m, 2H), 2.0(m, 2H), 2.42(s, 3H), 2.57(m, 1H), 2.76(td, 2H), 3.01(m, 4H), 3.69(m, 6H), 6.79(d, 1H), 7.36(d, 2H), 7.61(d, 2H), 8.26(d, 1H), 8.39(s, 1H) |
| 9 | Cl | N | N | H | 4-Br | 193 | 3.04(t, 4H), 3.16(t, 4H), 3.41(m, 8H), 6.78(d, 1H), 7.61(d, 2H), 7.68(d 2H), 8.32(d, 1H), 8.42(s, 1H) |

EXAMPLE 3

N-Chlorosuccinimide (3.06 g) was added to a stirred suspension of 1-(4-bromophenylsulphonyl)-4-[1-(4-pyridyl)piperazin-4-ylcarbonyl]piperazine (10.1 g) in acetonitrile (350 ml) at 20° C. The mixture was stirred for 48 hours and the acetonitrile evaporated. Water (200 ml) was added to the mixture and the aqueous phase was extracted with dichloromethane (3×200 ml). The organic extracts were combined, dried and evaporated, and the residue purified by column chromatography on silica gel, eluting with dichloromethane:methanol (97:3) to give a foam on evaporation. Trituration with diethyl ether (200 ml) gave 1-(4-bromophenylsulphonyl)-4-[1-(3-chloro-4-pyridyl)piperazin4-ylcarbonyl]piperazine as a cream-coloured solid (7.82 g): mp 194–195° C.: $^1$HNMR (CDCl$_3$); 3.04 (t, 4H), 3.18 (t, 4H), 3.42 (m, 8H), 6.78 (d, 1H), 7.91 (d, 2H), 7.70 (d, 2H), 8.34 (d, 2H), 8.42 (s, 1H); EI-MS m/z 528 (M+H).

The starting material was prepared as follows:

4-Pyridylpiperazine (18.5 g) was added to a stirred suspension of 4-nitrophenyl(4-t-butoxycarbonyl)piperazine-1-carboxylate (40 g) in DMF (450 ml). The reaction mixture was heated at 120° C. for 22 hours. The DMF was removed by evaporation and the residue triturated with water (500 ml) and dichloromethane (500 ml) added. The organic phase was washed with sodium hydroxide solution (6×250 ml) and saturated brine (2×250 ml), dried and evaporated. The residue was purified by chromatography on silica gel using a mixture of dichloromethane:methanol (97:3) as eluant to give a solid.

A solution of the above crude solid (20 g) in dichloromethane (120 ml) was treated at 5° C. with a solution of triflouroacetic acid (80 ml) in dichloromethane (40 ml). The reaction mixture was stirred for 2 hours. The solvent and excess triflouroacetic acid were removed in vacuo. The residue was treated with saturated brine solution (200 ml) and basified to pH 12 with 40% sodium hydroxide solution. The aqueous phase was extracted with dichloromethane (3×200 ml). The combined organic phases were washed with saturated brine solution, dried and evaporated to give, as an amber oil, 1-(4-pyridyl)piperazin-4-ylcarbonyl-1-piperazine (10.2 g): $^1$HNMR (CDCl$_3$): 2.90 (t, 4H), 3.32 (t, 4H), 3.38 (m, 8H), 6.65 (d, 2H), 8.30 (d, 2H); m/z 276 (M+H).

A solution of 4-bromophenylsulphonyl chloride (6.85 g) in dichloromethane (100 ml) was added dropwise to a stirred solution of the above piperazine derivative (7.34 g) in dichloromethane (100 ml) containing triethylamine (7 ml) over 10 minutes and the mixture stirred for 2 hours at 20° C.

The organic phase was washed with water, dried and evaporated. The residue was purified by chromatography on silica gel, eluting with a mixture of dichloromethane:methanol (95:5) to give, as a yellow solid, 1-(4-bromophenylsulphonyl)-4-[1-(4-pyridyl)piperazin-4-ylcarbonyl]piperazine (7.1 g): $^1$HNMR (CDCl$_3$): 3.04 (t, 4H), 3.32 (m, 12H), 6.62 (d, 2H), 7.58 (d, 2H), 7.68 (d, 2H), (d, 2H): m/z 494 (M+H).

EXAMPLE 4

In a similar manner to Example 3 were prepared the compounds described in Table 2

TABLE 2

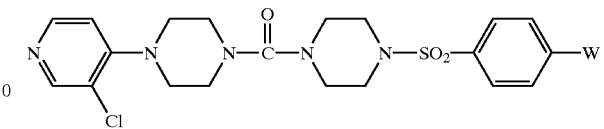

| Ex. | W | mp (° C.) | $^1$HNMR (CDCl$_3$) |
|---|---|---|---|
| A | 4-CF$_3$ | 159–160 | 3.06(t, 4H), 3.15(t, 4H), 3.40(t, 8H), 6.78(d, 1H), 7.82(d, 2H), 7.90(d, 2H), 8.33(d, 1H), 8.42(s, 1H) |
| B | 4-F | 143–144 | 3.04(t, 4H), 3.15(t, 4H), 3.41(t, 4H), 6.78(d, 1H), 7.21(d, 2H), 7.78(d, 2H), 8.33(d, 1H), 8.42(s, 1H) |
| C | 4-Cl | 162–163 | 3.04(t, 4H), 3.16(t, 4H), 3.40(m, 8H), 6.79(d, 1H), 7.52(d, 2H), 7.75(d, 2H), 8.32(d, 1H), 8.42(s, 1H) |

The following starting materials were isolated and characterised in an analogous manner to Example 3.

For A—A sandy-coloured solid, 1-(4-trifluoromethylphenylsulphonyl)-4-[1-(4-pyridyl)piperazin-4-ylcarbonyl]piperazine (6.0 g): $^1$HNMR (CDCl$_3$): 3.08(t, 4H), 3.30–3.40(m, 8H), 4.30–4.35(t, 4H), 6.63(d, 2H), 7.82 (d, 2h), 7.90(d, 2H), 8.30(d, 2h), EI-MS m/z 484(M+H).

For B—1-(4-Fluorophenylsulphonyl)-4-[1-(4-pyridyl)piperazin-4-yl)carbonyl]piperazine as a pale yellow solid (9.18 g): m.p. 143–144° C.: $^1$HNMR (CDCl$_3$): 3.04(t, 4H), 3.15(t,4H), 3.41(t, 8H), 6.78(d, 1H), 7.21(d, 2H), 7.78(m, 2H), 8.33(d, 1H), 8.42(s,H), EI-MS m/z 468(M+H).

For C—A sandy-coloured solid, 1-(4-chlorophenylsulphonyl)-4-[1-(4-pyridyl)piperazin-4-ylcarbony]piperazine (10.5 g) m.p. 184–186° C.; $^1$HNMR (CDCl$_3$): 3.03(t, 4H), 3.32(m, 8H), 3.42(t, 4H), 6.62(d, 2h), 7.52(d, 2H), 7.66(d, 2H), 8.30(d, 2H): EI-MS m/z 450 (M+H).

EXAMPLE 5

4-Bromophenylsulphonyl chloride (1.02 g) was added to a mixture of 1-[1-(3-fluoro-4-pyridyl)-piperidin-4-ylcarbonyl]piperazine hydrochloride (1.22 g) and triethylamine (3.70 ml) in dichloromethane (45 ml) at 0° C. The solution was stirred at ambient temperature for 18 hours. The solution was diluted with dichloromethane and washed with water, dried (Na$_2$SO$_4$) and evaporated. The residue was purified by chromatography eluting with 2% methanol in dichloromethane. Recrystallisation from ethyl acetate/hexane gave 1-(4-bromophenylsulphonyl)-4-[1-(3-fluoro-4-pyridyl)piperidin-4-ylcarbonyl]piperazine (1.24 g) as a solid.

Found C, 49.80; H 4.70 and N, 10.90%. C$_{21}$H$_{24}$BrFN$_4$O$_3$S requires C, 49.80; H, 4.70 and N, 11.00%. $^1$HNMR (CDCl$_3$): 1.70 (m, 2H), 1.90 (m, 2H), 2.60 (m, 1H), 2.85 (m, 2H, 3.00 (m, 4H), 3.70 (m, 6H), 6.70 (dd, 1H), 7.60 (d, 2H), 7.70 (d, 2H) 8.10 (d, 1H) and 8.20 (d, 1H); m/z 511 (M+1).

The starting material was prepared as follows:

To a solution of N-benzyloxycarbonyl isonipecotic acid (123.64 g) in tetrahydrofuran (300 ml) at 0° C. was added a solution of carbonyldiimidazole (68.80 g) in tetrahydrofuran (500 ml) and dichloromethane (300 ml). The resulting solution was stirred at ambient temperature for 2 hours. This solution was cooled to 0° C. and a solution of 1-(tert-butoxycarbonyl)piperazine (87.02 g) in tetrahydrofuran (200 ml) added dropwise over minutes. The suspension obtained was stirred at ambient temperature for 48 hours. Solvent was evaporated. The residue was dissolved in diethyl ether/dichloromethane (1500 ml) and washed with water, 2M aqueous citric acid solution, saturated aqueous sodium bicarbonate solution, dried ($Na_2SO_4$) and evaporated to give 1-(tert-butoxycarbonyl)-4-[1-benzyloxycarbonylpiperidin-4-ylcarbonyl]piperazine (180.00 g) as a solid.

$^1$HNMR ($CDCl_3$): 1.45 (s, 9H), 1.75 (m, 4H), 2.60 (m, 1H), 2.85 (m. 2H), 3.40 (m, 6H), 3.60 (m, 2H), 4.20 (m, 2H), 5.10 (s, 2H), and 7.35 (m, 5H); m/z 432 (M+1)

A solution of 1-(tert-butoxycarbonyl)-4-[1-benzyloxycarbonylpiperidin-4-ylcarbonyl]piperazine (41.31 g) in ethanol (1200 ml) was hydrogenated over 10% palladium-on-carbon for 18 hours. The reaction mixture was filtered through celite and solvent evaporated to give, 1-(tert-butoxycarbonyl)-4-(piperidin-4-ylcarbonyl) piperazine (18.95 g) as a solid.

$^1$HNMR ($CDCl_3$): 1.45 (s, 9H), 1.70 (m, 4H), 2.60 (m, 2H), 2.80 (m, 1H), 3.50 (m, 10H); m/z 298

To a suspension of 3-fluoro-4-iodopyridine (2.23 g), 1-(tert-butoxycarbonyl)-4-(piperidin-4-ylcarbonyl)piperazine (1.49 g) and sodium t-butoxide (1.06 g) in 1,4-dioxan (20 ml) was added tris(dibenzylidene acetone)dipalladium(0) (0.09 g) and tri-o-tolylphosphine (0.12 g) and the mixture heated at reflux for 3 hours. The mixture was diluted with diethyl ether and washed with saturated aqueous sodium chloride solution, dried ($Na_2SO_4$) and evaporated. The residue was purified by chromatography on alumina (N32–63) eluting with 0.4% methanol in dichloromethane to give as a solid, 1-(tert-butoxycarbonyl)-4-[1-(3-fluoro-4-pyridyl)piperidin-4-ylcarbonyl]piperazine (0.70 g).

$^1$HNMR ($CDCl_3$): 1.45 (s, 9H), 1.80 (m, 2H), 2.00 (m, 2H), 2.65 (m, 1H), 2.90 (m, 2H), 3.40 (m, 8H), 3.80 (m, 2H), 6.70 (dd, 1H), 8.10 (d, 1H) and 8.20 (d, 1H); m/z 393 (M+1).

Ethyl acetate (40 ml) saturated with gaseous HCl was added to a solution of 1-(tert-butoxycarbonyl)-4-[1-(3-fluoro-4-pyridyl)piperidin-4-ylcarbonyl]piperazine (2.60 g) in ethyl acetate (20 ml) and the resulting suspension stirred at ambient temperature for 3 hours. Solvent was evaporated to give 1-[1-(3-fluoro-4-pyridyl)piperidin-4-carbonyl]piperazine hydrochloride (2.45 g) as a solid.

EXAMPLE 6

4-Trifluoromethylphenylsulphonyl chloride (0.97 g) was added to a mixture 1-[1-(3-fluoro-4-pyridyl)piperidin-4-ylcarbonyl]piperazine hydrochloride (1.22 g) and triethylamine (3.70 ml) in dichloromethane (45 ml) at 0° C. The solution was stirred at ambient temperature for 18 hours. The solution was diluted with dichloromethane and washed with water, dried ($Na_2SO_4$) and evaporated. The residue was purified by chromatography eluting with 2% methanol in dichloromethane. Recrystallisation from ethyl acetate/hexane gave 1-(4-trifluoromethylphenylsulphonyl)-4-[1-(3-fluoro-4-pyridyl)piperidin-4-ylcarbonyl]piperazine (0.99 g) as a solid.

Found C, 52.90; H, 4.80 and N, 11.10%. $C_{22}H_{24}F_4N_4O_3S$ requires C, 52.80; H, 4.80 and N, 11.20%. $^1$HNMR ($CDCl_3$): 1.70 (m, 2H), 1.90 (m, 2H), 2.60 (m, 1H), 2.85 (m, 2H), 3.00 (m, 4H), 3.70 (m, 6H), 6.70 (dd, 1H), 7.80 (d, 2H), 7.90 (d, 2H) 8.10 (d, 1H) and 8.20 (d, 1H); m/z 501 (M+1).

The starting material was prepared as follows:

To a solution of N-benzyloxycarbonyl isonipecotic acid (123.64 g) in tetrahydrofuran (300 ml) at 0° C. was added a solution of carbonyldiimidazole (68.80 g) in tetrahydrofuran (500 ml) and dichloromethane (300 ml). The resulting solution was stirred at ambient temperature for 2 hours. This solution was cooled to 0° C. and a solution of 1-(tert-butoxycarbonyl)piperazine (87.02 g) in tetrahydrofuran (200 ml) added dropwise over 20 minutes. The suspension obtained was stirred at ambient temperature for 48 hours. Solvent was evaporated. The residue was dissolved in diethyl ether/dichloromethane (1500 ml) and washed with water, 2M aqueous citric acid solution, saturated aqueous sodium bicarbonate solution, dried ($Na_2SO_4$) and evaporated to give 1-(tert-butoxycarbonyl)-4-[1-benzyloxycarbonylpiperidin-4-ylcarbonyl]piperazine (180.00 g) as a solid.

$^1$HNMR ($CDCl_3$): 1.45 (s, 9H), 1.75 (m, 4H), 2.60 (m, 1H), 2.85 (m, 2H), 3.40 (m, 6H), 3.60 (m, 2H), 4.20 (m, 2H), 5.10 (s, 2H), and 7.35 (m, 5H); m/z 432 (M+1).

A solution of 1-(tert-butoxycarbonyl)-4-[1-benzyloxycarbonylpiperidin-4-ylcarbonyl]piperazine (41.31 g) in ethanol (1200 ml) was hydrogenated over 10% palladium-on-carbon for 18 hours. The reaction mixture was filtered through celite and solvent evaporated to give, 1-(tert-butoxycarbonyl)-4-(piperidin-4-ylcarbonyl) piperazine (18.95 g) as a solid.

$^1$HNMR ($CDCl_3$): 1.45 (s, 9H), 1.70 (m, 4H), 2.60 (m, 2H), 2.80 (m, 1H), 3.50 (m, 10H); m/z 298

To a suspension of 3-fluoro-4-iodopyridine (2.23 g), 1-(tert-butoxycarbonyl)-4-(piperidin-4-ylcarbonyl) piperazine (1.49 g) and sodium t-butoxide (1.06 g) in 1,4-dioxan (20 ml) was added tris(dibenzylidene acetone)dipalladium (0) (0.09 g) and tri-o-tolylphosphine (0.12 g) and the mixture heated at reflux for 3 hours. The mixture was diluted with diethyl ether and washed with saturated aqueous sodium chloride solution. dried ($Na_2SO_4$) and evaporated. The residue was purified by chromatography on alumina (N32–63) eluting with 0.4% methanol in dichloromethane to give as a solid, 1-(tert-butoxycarbonyl)-4-[1-(3-fluoro-4-pyridyl)piperidin-4-ylcarbonyl]piperazine (0.70 g).

$^1$HNMR ($CDCl_3$): 1.45 (s, 9H), 1.80 (m, 2H), 2.00 (m, 2H), 2.65 (m, 1H), 2.90 (m, 2H), 3.40 (m, 8H), 3.80 (m, 2H), 6.70 (dd, 1H), 8.10 (d, 1H) and 8.20 (d, 1H); m/z 393 (M+1).

Ethyl acetate (40 ml) saturated with gaseous HCl was added to a solution of 1-(tert-butoxycarbonyl)-4-[1-(3-fluoro-4-pyridyl)piperidin-4-ylcarbony]piperazine (2.60 g) in ethyl acetate (20 ml) and the resulting suspension stirred at ambient temperature for 3 hours. Solvent was evaporated to give 1-[1-(3-fluoro-4-pyridyl)piperidin-4-ylcarbonyl]piperazine hydrochloride (2.45 g) as a solid.

EXAMPLE 7

N-Chlorosuccinimide (3.63 g) was added to a stirred solution of 1-(4-trifluoromethylphenylsulphonyl)-4-[1-(4-pyridyl)piperazin-4-ylcarbonyl]piperazine (12.0 g) in acetonitrile (380 mL) at 20° C. The mixture was stirred for 48 hours and the acetonitrile evaporated. Water (200 mL) was added to the mixture and the aqueous phase was extracted with dichloromethane (3×200 mL). The organic extracts were combined, dried and evaporated. The residue was purified by column chromatography on silica gel, eluting with a mixture of dichloromethane:methanol (97.5:2.5) to give a foam on evaporation. Trituration with diethyl ether (250 mL) gave 1-(4-trifluorophenylsulphonyl)-4-[1-(3-chloro-4-pyridyl)piperazin-4-ylcarbonyl]piperazine as a pale yellow solid (7.32 g); mp 159–160° C.; microanalysis found: C, 48.6; H, 4.2; N, 13.1% $C_{21}H_{23}N_5ClF_3O_3S$ requires: C, 48.6; H 4.4; N, 13.5%; NMR: (CDCl$_3$); 3.04(t, 4H), 3.18(t, 4H), 3.40(t, 8H), 6.78(d, 1H), 7.82(d, 2H), 7.90(d, 2H), 8.33(d, 1H), 8.42(s, 1H); EI-MS m/z 518 (M+H).

The starting material was prepared as follows:

A solution of 4-trifluoromethylphenylsulphonyl chloride (6.62 g) in dichloromethane (5 mL) was added dropwise over 10 minutes to a stirred solution of 1-[1-(4-pyridyl) piperazin-4-ylcarbonyl]piperazine (5.7 g) (prepared as in Example 1) in dichloromethane (50 mL) containing triethylamine (6 mL) at 20° C. The reaction mixture was stirred for 2 hours at 20° C. The organic phase was washed with water (3×100 mL) and saturated brine solution (2×100 mL) dried and evaporated. The residue was purified by chromatography on silica gel, eluting with a mixture of dichloromethane: methanol (95:5) to give, as a sandy-coloured solid, 1-(4-trifluoromethylphenylsulphonyl)-4-[1-(4-pyridyl)piperazin-4-ylcarbonyl]piperazine (6.0 g): NMR (CDCl$_3$): 3.08(t, 4H), 3.30–3.40 (m, 8H), 3.40–3.45(t, 4H), 6.63(d, 2H), 7.82(d, 2H), 7.90(d, 2H), 8.30(d, 2H); EI-MS m/z 484(M+H).

EXAMPLE 8

N-Chlorosuccinimide (4.05 g) was added to a stirred suspension of 1-(4-fluorophenylsulphonyl)-4-[1-(4-pyridyl) piperazin-4-ylcarbonyl]piperazine (12.45 g) in acetonitrile (500 mL) at 20° C. The mixture was stirred for 48 hours and the acetonitrile evaporated. Water (200 mL) was added to the residue and the aqueous phase extracted with dichloromethane (3×200 mL). The organic extracts were dried and evaporated. The residue was purified by column chromatography on silica gel, eluting with dichloromethane:methanol (97:3) to give a foam on evaporation. Trituration with diethyl ether (250 mL) gave 1-(4-fluorophenylsulphonyl)-4-[1-(3-chloro-4-pyridyl)piperazin-4-ylcarbonyl]piperazine as a pale yellow solid (9.18 g): mp 143–144° C.: NMR (CDCl$_3$): 3.04(t, 4H), 3.15(t, 4H), 3.41(t, 8H), 6.78(d, 1H), 7.21(d, 2H), 7.78(m, 2H), 8.33(d, 1H), 8.42(s, 1H); EI-MS m/z 468(M+H).

The starting material was prepared as follows:

A solution of 4-fluorophenylsulphonyl chloride (7.8 g) in dichloromethane (100 mL) was added to a stirred solution of 1-[1-(4-pyridyl)piperazin-4-ylcarbonyl]piperazine (11.0 g) (prepared as in Example 1) in dichloromethane (100 mL) containing triethylamine (12 mL) at 20° C. The mixture was stirred for 2 hours at 20° C. The organic phase was washed with water (3×100 mL) and saturated brine solution (2×100 mL), dried, filtered and evaporated. The residue was purified by column chromatography on silica gel, eluting with dichloromethane:methanol (97:3) to give as a salmon-coloured solid, 1-(4-flurophenylsulphonyl4-[1-(4-pyridyl) piperazin-4-ylcarbonyl]piperazine (12.45 g): NMR (CDCl$_3$): 3.04(t, 4H), 3.39(m, 12H), 6.63(d, 2H), 7.23(m, 2H), 7.77(m, 2H), 8.30(d, 2H); EI-MS m/z 434 (M+H).

EXAMPLE 9

Phenylsulphonyl chloride (0.38 g) was added to a mixture of 1-[(3-fluoro-4-pyridyl)piperazin-4-ylcarbonyl]piperazine dihydrochloride (0.65 g) and triethylamine (1.5 ml) in dichloromethane (30 ml) at 5° C. The solution was stirred at 5° C. for 1 hour and at ambient temperature for 18 hours. The solution was evaporated to dryness. The residue was dissolved in dichloromethane (100 ml), and the solution was washed with water (3×10 ml), dried (Na$_2$SO$_4$) and evaporated. The residue was purified by chromatography on alumina (N32–63) using 0.1–0.3% methanol in dichloromethane as eluent. Recrystallisation from ethyl acetate/ isohexane gave 1-phenylsulphonyl-4-[1-(3-fluoro-4-pyridyl)piperazin-4-ylcarbonyl]piperazine (0.49 g), as an off-white solid mp 143–145° C: NMR (CDCl$_3$): 3.05 (t, 4H), 3.25 (t, 4H), 3.40 (m, 8H), 6.70 (dd, 1H), 7.60 (m, 3H), 7.78 (s, 2H), 8.20 (dd, 2H); m/z 434 (M+1).

The starting material was prepared as follows:

A solution of 3-fluoropyridine (19.4 g) in dry tetrahydrofuran (20 ml) was added dropwise over 30 minutes, under an atmosphere of argon, to a stirred solution of 2M lithium diisopropylamide/tetrahydrofutran/heptane (100 ml) in dry tetrahydrofuran (700 ml) at −70° C. The mixture was stirred at −70° C. for 4 hours. A solution of iodine (50.7 g) in dry tetrahydrofuran (160 ml) was added dropwise to this stirred suspension at −70° C. over 45 minutes and stirring was continued for a further 45 minutes. A mixture of tetrahydrofuran (160 ml)/water (40 ml) was added to the resulting solution at −70° C. The solution was allowed to warm to 0° C. Water (200 ml) was added and diethyl ether (400 ml). The mixture was allowed to stand at ambient temperature for 16 hours. The ether layer was separated. The aqueous layer was extracted with ether (2×100 ml). The ether layers were all combined, washed with aqueous sodium thiosulphate solution (2×250 ml) and saturated brine (2×100 ml), dried (Na$_2$O$_4$) and evaporated to low bulk. The residue was dissolved in dry diethyl ether and the solution was cooled to −50° C. The solid, which had separated, was filtered off and washed with pentane at −50° C. to give 3-fluoro-4-iodopyridine (22.8 g) as a white solid: NMR (CDCl$_3$): 7.75 (t, 1H), 8.05 (d, 1H), 8.3 5 (s, 1H); m/z 223 M.

Tris(dibenzylideneacetone)dipalladium(0) (0.184 g) and tri-o-tolylphosphine (0.244 g) were added to a suspension of 3-fluoro-4-iodopyridine (4.46 g), 1-[1-(t-butoxycarbonyl) piperazin-4-ylcarbonyl]piperazine (3.0 g) and sodium t-butoxide (2.12 g) in dry 1,4-dioxane (40 ml) under an atmosphere of argon. The mixture was heated at 100° C. for 18 hours. The mixture was cooled, diluted with diethyl ether (200 ml) and washed with saturated brine (40 ml). The aqueous layer was back-extracted with diethyl ether (2×100 ml). The ether layers were all combined, washed with saturated brine (2×100 ml), dried (Na$_2$SO$_4$) and evaporated. The residual oil was purified by chromatography on alumina (N32–63) using 0.1–0.4% methanol in dichloromethane as eluent to give 1-(t-butoxycarbonyl)-4-[1-(3-fluoro-4-pyridyl)piperazin-4-ylcarbonyl]piperazine (1.7 g) as an orange solid: NMR (CDCl$_3$): 1.47 (s, 9H), 3.25 (m, 8H), 3.45 (m, 8H), 6.75 (dd, 1H), 8.20 (dd, 2H); m/z 394 (M+1).

Ethyl acetate saturated with gaseous HCl (35 ml) was added to a solution of 1-(t-butoxycarbonyl)-4-[11-(3-fluoro-4-pyridyl)piperazin-4-ylcarbonyl]piperazine (1.6 g) in ethyl acetate (I16 ml). The resulting suspension was stirred vigorously at ambient temperature for 3 hours. The solvent was evaporated to give 1-[1-(3-fluoro-4-pyridyl)piperazin-4-ylcarbonyl]piperazine dihydrochloride (0.65 g) as a cream solid.

EXAMPLE 10

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| (a) Tablet I | mg/tablet |
|---|---|
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium Stearate | 1.0 |

| (b) Tablet II | mg/tablet |
|---|---|
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| | mg/tablet |
|---|---|
| (c) Tablet III | |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule | |
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples. The tablet compositions (a)–(c) may be enteric coated by conventional means, for example, with cellulose acetate phthalate.

FORMULAE

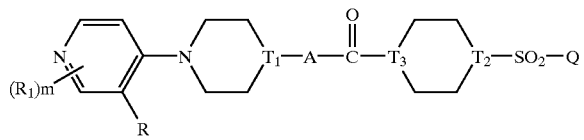

I

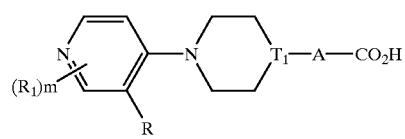

II

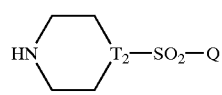

III

IV

FORMULAE

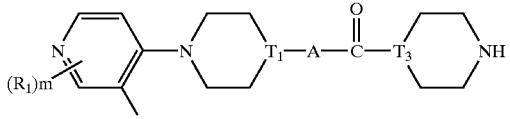

V

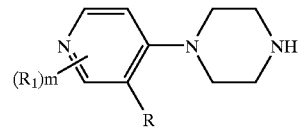

VI

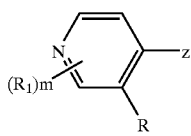

VII

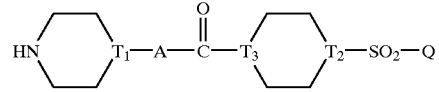

VIII

What is claimed is:
1. A compound of formula I, or a pharmaceutically acceptable salt thereof

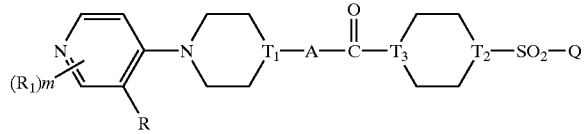

I wherein:
R is selected from halogeno, cyano, nitro, carboxy, (1–6C)alkyl, (1–6C)alkoxy, (1–6C)alkanoyl, (1–6C)alkoxycarbonyl and halogeno(1–6C)alkyl;
$R_1$ is selected from hydrogen, amino, halogeno, cyano, nitro, carboxy, (1–6C)alkyl, (1–6C)alkoxy, (1–6C)alkanoyl, (1–6C)alkoxycarbonyl, halogeno(1–6C)alkyl, N-(1–6C)alkylamino, N,N-di-[(1–6C)alkyl]amino, (1–6C)alkylthio, (1–6C)alkylsulphinyl and (1–6C)alkylsulphonyl;
m is 1 or 2;
A is selected from a direct bond and (1–4C)alkylene;
$T_1$, $T_2$ and $T_3$ are each N;
wherein the heterocyclic ring containing $T_1$ and the heterocyclic ring containing $T_2$ may, independently, be optionally substituted by one or more substituents selected from (1–6C)alkyl, (1–6C)alkoxy, phenyl (1–4C)alkyl, halogeno and (1–6C)alkoxycarbonyl; and
Q is selected from a heteroaryl moiety containing up to 3 heteroatoms selected from nitrogen, oxygen and sulphur, or from phenyl, naphthyl, phenyl(1–6C)alkyl and phenyl(2–6C)alkenyl;

and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cycloalkyl(1–4C)alkyl, (1–4C)alkylenedioxy, (1–6C)alkylamino, N,N-di-[(1–6C)alkyl]amino, N-(1–6C)alkylcarbamoyl, di-N[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, (1–6C)alkanoyl and a heteroaryl group comprising a 5- or 6-membered monocyclic heteroaryl ring containing up to three heteroatoms selected from nitrogen, oxygen and sulphur.

2. A compound of formula I, or a pharmaceutically-acceptable salt thereof—according to claim 1 wherein Q is phenyl, napthyl, or phenyl (2–6C)alkenyl.

3. A compound of formula I, or a pharmaceutically-acceptable salt thereof, according to claim 2 wherein Q is phenyl.

4. A compound of formula I, or a pharmaceutically-acceptable salt thereof, according to any one of claims 1 or 2–3, wherein R is selected from halogeno and halogeno (2–6C)alkyl.

5. A compound of formula I or a pharmaceutically-acceptable salt thereof, according to any one of claims 1 or 2–3, wherein $R_1$ is selected from hydrogen, amino, (1–6C) alkyl and halogeno.

6. A compound of formula I or a pharmaceutically-acceptable salt thereof according to claim 5 wherein $R_1$ is hydrogen.

7. A compound of formula I or a pharmaceutically-acceptable salt thereof according to any one of claims 1 or 2–3 wherein A is a direct bond.

8. A compound of formula I or a pharmaceutically-acceptable salt thereof according to any one of claims 1 or 2–3 wherein Q is substituted by at least one substituent selected from halogeno, (1–6C)alkoxy, (1–6C)alkyl, halogeno(1–6C)alkyl, N,N-di-[(1–4C)alkyl]amino, nitro, cyano, and (1–6C)alkanoylamino.

9. A compound or a pharmaceutically-acceptable salt thereof selected from:
1-(4-trifluoromethylphenylsulphonyl)-4-[1-(3-chloro-4-pyridyl)piperazin-4-carbonyl]piperazine;
1-(4-fluorophenylsulphonyl)-4-[1-(3-chloro-4-pyridyl)piperazin-4-ylcarbonyl]piperazine; and
1-phenylsulphonyl-4-[1-(3-fluoro-4-pyridyl)piperazin-4-ylcarbonyl]piperazine.

10. A pharmaceutical composition comprising a compound of formula according to any one of claims 1 and 2–3 or a pharmaceutically-acceptable salt thereof and a pharmaceutically-acceptable diluent or carrier thereof.

11. A method for the treatment of hypercholesterolemia or atheromatous vascular degeneration in a warm blooded animal in need thereof, said method comprising administering to said animal a treatment effective amount of a compound according to any one of claims 1 and 2–3, or a pharmaceutically acceptable salt thereof.

12. A method for treating hypercholesterolemia associated with atheromatous vascular degeneration in a warm-blooded animal requiring such treatment, which method comprises administering to such animal an effective amount of a compound of formula I or a pharmaceutically-acceptable salt thereof, as defined in any one of claims 1 or 2–3.

13. A method for treating an ischemic disease associated with atheromatous vascular degeneration in a warm blooded animal in need thereof, said method comprising administering to said animal an effective amount of a compound according to any one of claims 1 and 2–3, or a pharmaceutically acceptable salt thereof.

14. A process for the preparation of compounds of formula I as defined by claim 1, by:

(a) when $T_3$ is N, reacting an acid of formula II:

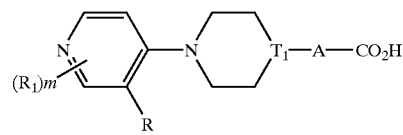

wherein $R_1$, m, R and $T_1$ are defined in claim 1, with an amine of formula III, or a reactive derivative thereof

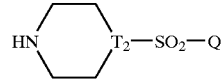

wherein $T_2$ and Q are defined in claim 1;

(b) when $T_2$ is N, reacting an amine of formula IV

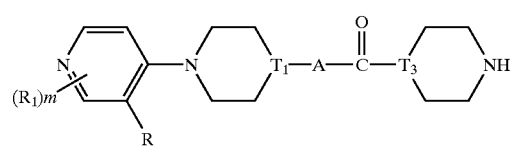

wherein $R_1$, m, R, T, A and $T_3$ are defined in claim 1, with a compound of formula

wherein Z is a displaceable group and Q is as defined in claim 1;

(c) when $T_1$ is N and wherein A is a direct bond, reacting a compound of formula V:

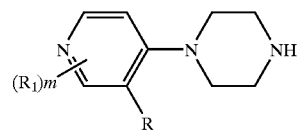

wherein $R_1$, m and R are as defined in claim 1, with a compound of formula VI or a reactive derivative thereof

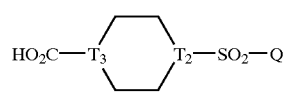

wherein $T_3$, $T_2$ and Q are as defined in claim 1;

(d) reacting a compound of formula VI

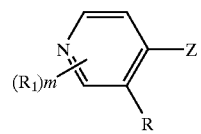

in which Z is a displaceable group and $R_1$, m and R are as defined in claim 1, with an amine of formula VII (e) when R is halogeno, halogenating the corresponding compound of formula I wherein R is hydrogen.

* * * * *